(12) United States Patent
Ganapathiappan et al.

(10) Patent No.: US 8,808,439 B2
(45) Date of Patent: Aug. 19, 2014

(54) PHTHALOCYANINES AND NAPHTHALOCYANINES WITH NEAR-IR ABSORPTIONS FOR INKJET INKS

(75) Inventors: Sivapackia Ganapathiappan, Los Altos, CA (US); Jayprakash Bhatt, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 248 days.

(21) Appl. No.: 13/383,724

(22) PCT Filed: Jul. 31, 2009

(86) PCT No.: PCT/US2009/052437
§ 371 (c)(1),
(2), (4) Date: Jan. 12, 2012

(87) PCT Pub. No.: WO2011/014190
PCT Pub. Date: Feb. 3, 2011

(65) Prior Publication Data
US 2012/0137928 A1 Jun. 7, 2012

(51) Int. Cl.
C09D 11/02 (2014.01)
C09B 47/12 (2006.01)
C09B 47/18 (2006.01)
C09B 47/20 (2006.01)
C09B 47/22 (2006.01)
C09B 47/24 (2006.01)

(52) U.S. Cl.
USPC ............... 106/31.49; 106/31.28; 540/129; 540/132; 540/133; 540/135; 540/139; 540/140

(58) Field of Classification Search
CPC ............ C09D 11/328; C09B 47/0673; C09B 47/0675; C09B 47/0676; C09B 47/0678
USPC ............ 106/31.49, 31.28; 540/129, 132, 133, 540/135, 139, 140
See application file for complete search history.

(56) References Cited

U.S. PATENT DOCUMENTS

| | | | |
|---|---|---|---|
| 5,618,929 A * | 4/1997 | Harrison et al. | 540/139 |
| 5,618,930 A | 4/1997 | Kimura et al. | |
| 5,763,601 A | 6/1998 | Shirai et al. | |
| 7,322,927 B2 | 1/2008 | Buechler et al. | |
| 7,579,064 B2 * | 8/2009 | Vonwiller et al. | 106/31.49 |
| 8,226,757 B2 * | 7/2012 | Ganapathiappan et al. | 106/31.49 |
| 2005/0073563 A1 | 4/2005 | Hanaki et al. | |
| 2007/0008393 A1 | 1/2007 | Vonwiller et al. | |
| 2007/0279468 A1 | 12/2007 | Kinas et al. | |
| 2008/0199732 A1 * | 8/2008 | Lee et al. | 540/139 |
| 2011/0204234 A1 * | 8/2011 | Ganapathiappan et al. | 540/131 |
| 2012/0139994 A1 * | 6/2012 | Ganapathiappan et al. | 106/31.49 |

FOREIGN PATENT DOCUMENTS

| | | | |
|---|---|---|---|
| CN | 101248142 A | | 8/2008 |
| EP | 1304359 A1 | | 4/2003 |
| JP | 01/045386 | * | 2/1989 |
| JP | 1045386 A | | 2/1989 |
| JP | 01/061289 | * | 3/1989 |
| JP | 1061289 A | | 3/1989 |
| JP | 2000/353553 | * | 12/2000 |
| JP | 200353553 A | | 12/2000 |
| WO | WO-2007002981 A1 | | 1/2007 |
| WO | WO 2010/050962 A1 | * | 5/2010 |
| WO | WO-2010050962 A1 | | 5/2010 |
| WO | WO-2010151264 A1 | | 12/2010 |

OTHER PUBLICATIONS

European Search Report. (Dec. 19, 2012) Hewlett-Packard Development Company, L.P.. European Application No. 09847932.2, filed Jan. 16, 2012.

* cited by examiner

Primary Examiner — Helene Klemanski
(74) Attorney, Agent, or Firm — David W. Collins

(57) ABSTRACT

A water-soluble phthalocyanine dye or naphthalocyanine dye with near-infrared absorption comprises at least one complexed unit. Each unit comprises a phthalocyanine or a naphthalocyanine moiety and a metal atom complexed thereto and having a valency of at least three, with two valencies complexed to the phthalocynanine ring or the naphthalocyanine ring, each unit joined to another through a fused ring, at least one valency attached to water-soluble axial ligands. The dyes to may be employed in inkjet inks in conjunction with colorants.

15 Claims, No Drawings

PHTHALOCYANINES AND NAPHTHALOCYANINES WITH NEAR-IR ABSORPTIONS FOR INKJET INKS

BACKGROUND ART

Inkjet printers are now very common and affordable and allow one to obtain decent print quality. They are used in home printing, office printing and commercial printing. In inkjet printers, print heads are used to eject ink droplets very accurately to place them on a desired location on a medium. The print head normally comprises a large number of nozzles, often, more than 400 nozzles. As a general rule, the larger the number of nozzles, the greater is the improvement of the print quality and speed. Frequently, the nozzles become blocked because of the usage of pigmented inks or inks containing particles. Sometimes, one or more nozzle orifices is may contain dried ink and fresh ink cannot be ejected. One result of this condition is the formation of streaks, which lead to poor print quality.

Near-infrared (near-IR) absorbing dyes may be added to the ink to monitor the condition of the nozzles. Other applications for such dyes exhibiting absorption in the near-IR include security printing, counterfeit assessment, RFID tags, etc. Near-IR absorbing dyes may be employed by extending the conjugation so that the absorption can be shifted to the range of 700 to 1000 nm range.

Many of the technologies utilizing near-IR materials require that these materials be dissolved in organic solvents, water and aqueous or organic solvent blends. Some applications, such as thermal inkjet printing require that the near-IR absorbing material be kept in aqueous solution for long periods of time. Near-IR dyes have to be stable in aqueous solvent blends for a long time without undergoing any kind of chemical change. Any degradation or changes to its physical/chemical nature can destroy the conjugation and thus lose the near-IR absorption. Such changes could adversely affect the desired property (absorption in the near-IR wavelength range) and cannot be used in such applications. Near-IR dyes of the Cyanine dye class are soluble in water but are chemically unstable in aqueous solutions over long time at wide pH range and are therefore not suitable for inkjet applications requiring aqueous solution stability for long time.

Phthalocyanine (PC) and naphthalocyanine (NPC) (metal free or metal complex) are chemically stable but are difficult to solubilize in water. Highly ionic groups or water-soluble ethylene oxide groups have to be attached for dissolving these compounds in water. These compounds are solubilized by attaching water-soluble groups on the benzene rings. But introduction of such groups changes the peak absorption dramatically up to 60 nm.

DETAILED DESCRIPTION

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the context clearly dictates otherwise.

As used herein, "vehicle" or "liquid vehicle" is defined to include liquid compositions that can be used to carry colorants to a substrate. Liquid vehicles are well known in the art, and a wide variety of ink vehicles may be used in accordance with embodiments of the present invention. Such ink vehicles may include a mixture of a variety of different agents, including without limitation, surfactants, organic solvents and co-solvents, buffers, biocides, viscosity modifiers, sequestering agents, stabilizing agents, anti-kogation agents, and water. Though not part of the liquid vehicle per se, in addition to the colorants, the liquid vehicle can carry solid additives such as polymers, latexes, UV curable materials, plasticizers, salts, etc. As such, the term "aqueous liquid vehicle" or "aqueous vehicle" refers to a liquid vehicle having water as a major solvent, and often, a predominant solvent.

The term "near infrared" or "near-IR" refers to optical radiation in the range of about 700 nm to 1400 nm. In accordance with embodiments of the present invention, the near-IR dyes of the present disclosure can absorb optical radiation within the near-IR spectrum, and in one embodiment, in the 700 nm to 1000 nm range.

As used herein, "colorant" can include dyes, pigments, and/or other particulates that may be suspended or dissolved in an ink vehicle prepared in accordance with embodiments of the present invention. Dyes are typically water-soluble, and therefore, can be desirable for use in many embodiments. However, pigments can also be used in other embodiments. Pigments that can be used include self-dispersed pigments and polymer dispersed pigments. Self-dispersed pigments include those that have been chemically surface modified with a charge or a poly-grouping. This chemical modification aids the pigment in becoming and/or substantially remaining dispersed in a liquid vehicle. The pigment can also be a polymer-dispersed pigment that utilizes a dispersant (which can be a polymer, an oligomer, or a surfactant, for example) in the liquid vehicle and/or in the pigment that utilizes a physical coating to aid the pigment in becoming and/or substantially remaining dispersed in a liquid vehicle. It is noted that the term "colorant" does not include the near-IR dyes described in accordance with embodiments of the present disclosure, e.g., near-IR dyes generally described in Formulae I-V.

The term "about" when referring to a numerical value or range is intended to encompass the values resulting from experimental error that can occur when taking measurements.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Numerical values, such as ratios, concentrations, amounts, molecular sizes, etc., may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight range of about 1 wt % to about 20 wt % should be interpreted to include not only the explicitly recited concentration limits of 1 wt % to about 20 wt %, but also to include individual concentrations such as 2 wt %, 3 wt %, 4 wt %, and sub-ranges such as 5 wt % to 15 wt %, 10 wt % to 20 wt %, etc.

As indicated above, current near-IR absorbing compounds are either not soluble in water or not very stable in water or inks. Methods for making such compounds are also difficult. In accordance with the teachings herein, the synthesis of near-IR absorbing compounds that are water-soluble or dispersed and that are very stable in water and other solutions such as inkjet ink formulation with a wide range of pH is improved. Only a small quantity has to be used for the desired application as these compounds exhibit very strong absorption in the near-IR region. These compounds are very soluble because of the presence of water-soluble group(s) such as ethylene oxides on the axial position of the central metal atom. Other water solubilizing groups are phosphates, sulfates, ammonium salts, amides, ethylene oxides, propylene oxides, ethylene sulfide, and propylene sulfide. Moreover, these compounds are also very stable because of the rigid PC and NPC ring network.

The water-soluble phthalocyanine dyes or naphthalocyanine dyes with near-infrared absorption comprise at least one complexed unit. Each unit comprises a phthalocyanine or a naphthalocyanine moiety and a metal atom complexed thereto. Each metal atom has a valency of at least three, with two valencies complexed to the phthalocynanine ring or the naphthaiocyanine ring. Each unit is joined to another through a fused ring, with at least one valency attached to water-soluble axial ligands.

There are two primary embodiments associated with the inks disclosed herein. In the first primary embodiment, unique water-soluble fused PC and NPC dye chromophores with solubilizing groups attached to the central metal atom are provided. In the second primary embodiment, unique water-soluble PC and NPC dye chromophores having extended conjugation with solubilizing groups attached to the central metal atom are provided. These two embodiments, and variants thereof, are discussed below.

A. Water-Soluble Fused PC and NPC Dye Chromophores with Solubilizing Groups Attached to the Central Metal Atom The fused phthalocyanine and naphthalocyanine compounds with axial water-soluble groups are water-soluble or dispersible in aqueous solutions or aqueous blend solutions and are stable over a wide pH range. These dyes exhibit absorptions in the near-infrared range 700 to 1000 nm. They find applications in a wide variety of fields, including security applications, printing, print authenticity, counterfeit assessment, RFID tags etc.

In accordance with some embodiments, unique water-soluble fused PC and NPC dye chromophores with solubilizing groups attached to the central metal atom are provided. For example, indium has a valency of three, with two valencies involved with NPC ring and the third one can be used to attach water-soluble groups such as ethylene oxide, ethylene sulfide, and propylene sulfide, sulfates or sulfonates.

These compounds have fused rings with PCs and NPCs and can be called as dimers, trimers or tetramers, for example, depending upon the number of PCs or NPCs attached. The higher the conjugation, results in a shift in the absorption at higher wavelength. This provides a choice of selection of dyes for the desired range. At the same time, functional groups can be incorporated to make the reaction smoother and at a lower temperature.

The present embodiments are directed to the design and synthesis of unique water-soluble oligomeric PC and NPC dye chromophores. Water-soluble oligomeric or poly(phthalocyanines) and poly(naphthalocyanines) dye chromophores are chemically stable in water as well as aqueous solvent blends at wide pH range and are well-suited for water-based inkjet ink applications.

The general structures of water-soluble dyes are disclosed in which the water-soluble groups are present as axial ligands on the central metal atom. Some suitable structures are shown here. The general structure of fused PC and NPC's are summarized below as shown in Formulae (I)-(III) below.

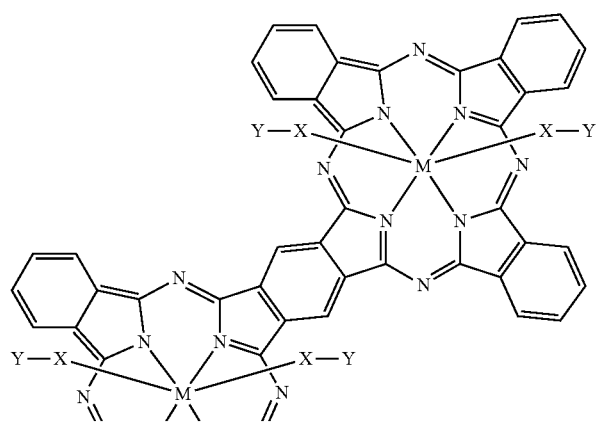

(I)

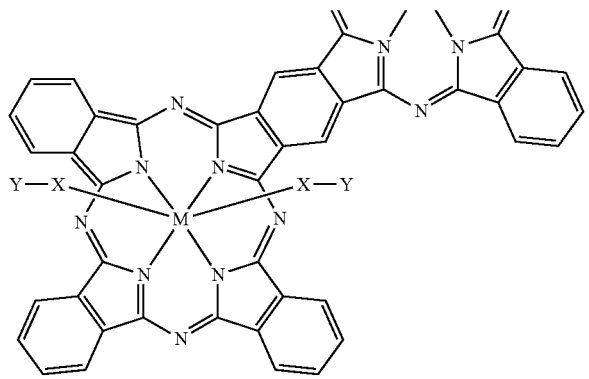

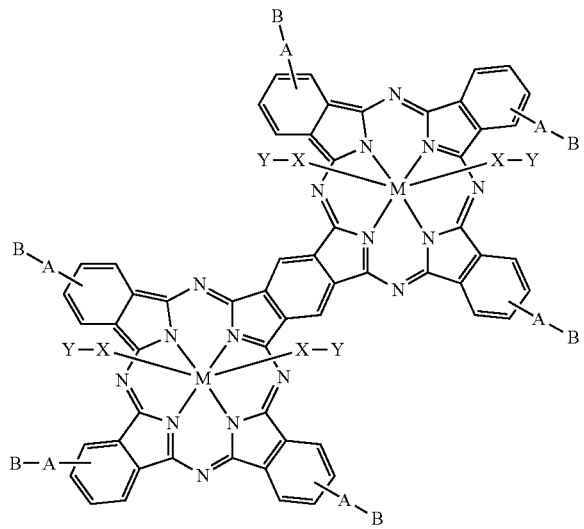

(II)

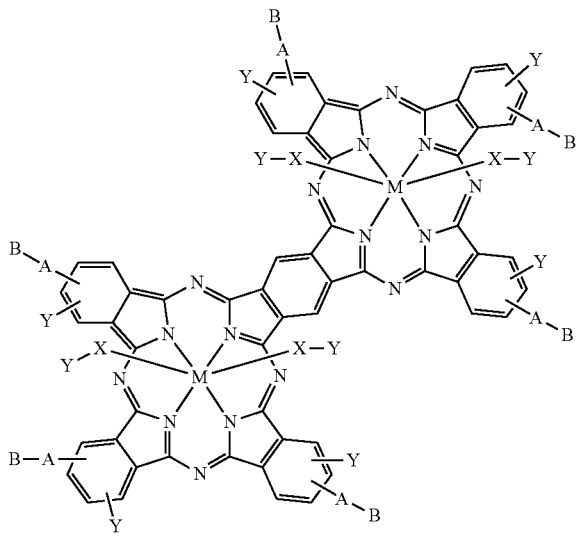

(III)

where:
X=single bond, O(CH$_2$)$_n$(n=1 to 20), O or NH;
Y=COOZ, SO$_3$Z, PO$_3$Z, NR$_4^+$, (CH$_2$CH$_2$O)$_m$CH$_3$, (CH$_2$CH(CH$_3$)O)$_m$, CH$_3$, (CH$_2$CH$_2$S)$_m$CH$_3$ or (CH$_2$CH(CH$_3$)S)$_m$CH$_3$ (m=1 to 500);
Z=H, monovalent metal ions;
A=divalent linking group;
B=H, alkyl or substituted alkyl;
the number of X-Y groups depends upon the valency of the metal atom M (if M is trivalent, then only one X-Y group is present; if M is tetravalent, then two X-Y groups are present); and
M=any metal from the periodic table with valency greater than 2

Examples of monovalent metal ions include, but are not limited to, Na$^+$, K$^+$, and NR$_4^+$.

Examples of divalent linking groups include, but are not limited to, O, CH$_2$, NH, COO, CONH, CO, SO$_3$, and SO$_2$NH.

Examples of M include indium, gallium, thallium, germanium, tin, antimony, bismuth, cobalt, nickel, silicon, titanium, titanyl, vanadium, vanadyl, chromium, manganese, yttrium, scandium, zirconium, niobium, molybdenum, ruthenium, rhodium, hafnium, tantalum, and bismuth.

The water-soluble phthalocyanine dye or naphthalocyanine dye with near-infrared absorption comprises from two to four complexed units, each unit comprising a phthalocyanine or a naphthalocyanine moiety. For example, Formula (I) has three such units, while Formulae (II) and (III) have two each. It will be seen that each unit is joined to an adjacent unit through a fused ring. The fusion in the trimer of Formula (I) is shown here through opposite side of the benzene rings. In addition, the fusing of benzene rings can be adjacent to each other. Moreover, the benzene ring can be replaced by naphthyl ring also as well as the two PC or NPC rings can be fused with naphthyl ring by using tetra substituted naphthalene derivative, for example 2,3,6,7-tetracyanonaph-thalene, as one of the components.

A metal atom is complexed to each unit, and each metal atom has a valency of at least three. Two valencies are used in complexing to the phthalocynanine ring or the naphthalocyanine ring. Where the metal atom has a valency of three, this leaves one valency for attachment to a water-soluble ligand. Where the metal atom has a valency of four, this leaves two valencies for attachment, each to a water-soluble ligand (Formulae (I)-(III)).

Further, Y moieties may be attached to the outermost benzene rings of the PC or NPC group, as shown in Formula (III). These Y moieties increase the water solubility further.

General Synthetic Process:

First, the fused PC or NPC derivative is formed with the central metal M with axial halogen atom(s), hydroxyl or alkoxy groups. Next, it is treated with the water solubilizing groups by nucleophilic substitution reactions, for example sulfuric acid, polyethylene glycols and the like materials. Then the product is purified by conventional purification processes such as column chromatography or crystallization techniques.

It can also be prepared in a single step using suitable ligands containing metal compounds.

B. Water-Soluble PC and NPC Dye Chromophores Having Extended Conjugation with Solubilizing Groups Attached to the Central Metal Atom The PC and NPC compounds having extended conjugation with water-soluble axial ligands are water-soluble or dispersible in aqueous solutions or aqueous blend solutions and are stable over a wide pH range. These dyes exhibit absorptions in the near-infrared range 700 to 1000 nm. They find applications in a wide variety of fields, including security applications, printing, print authenticity, counterfeit assessment, RFD tags etc.

In accordance with some embodiments, unique water-soluble PC and NPC dye chromophores having extended conjugation with solubilizing groups attached to the central metal atom are provided. For example, indium has a valency of three. Two of them are involved with NPC ring and the third one can be used to attach water-soluble groups such as ethylene oxide or sulfonates.

These unique water-soluble PC and NPC dye chromophores have extended conjugation so that near-IR absorptions can be from 700 to 1000 nm range. These dyes are chemically stable in water as well as aqueous solvent blends over a wide pH range and are well-suited for water-based inkjet ink applications.

The general structures of the water-soluble dyes include water-soluble groups present as axial ligands on the central metal atom. The general structures of NPC's with extended conjugation are summarized below as shown in Formulae (IV)-(V) below.

(IV)

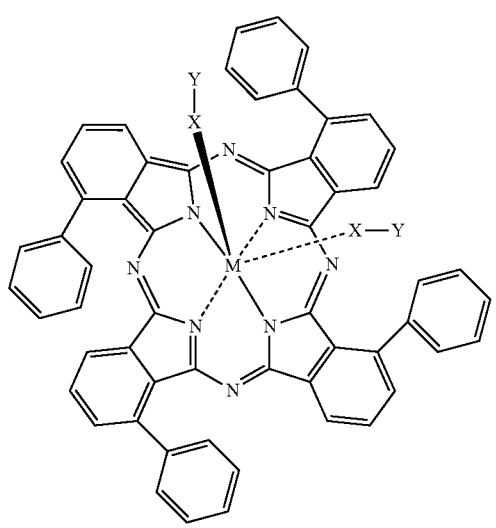

(V)

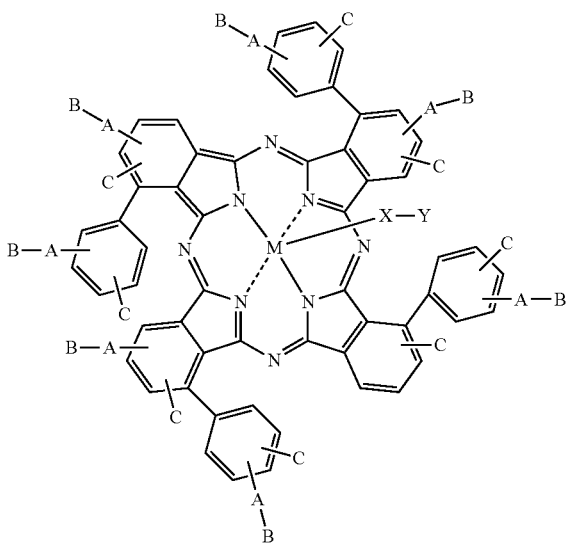

where:
X=single bond, O or NH;
Y=COOZ, $SO_3Z$, $PO_3Z$, $NR_4^+$, $(CH_2CH_2O)_mCH_3$, $(CH_2CH(CH_3)O)_mCH_3$, $(CH_2CH_2S)_mCH_3$ or $(CH_2CH(CH_3)S)_mCH_3$ (m=1 to 500);
Z=H, monovalent metal ions (e.g. $Na^+$, $K^+$) or $NR_4^+$;
A=divalent linking group (e.g., O, $CH_2$, NH, COO, CONN, CO, $SO_3$, $SO_2NH$);
B=C=H, alkyl or substituted alkyl;
the number of X-Y groups depends up on the valency of the metal atom M (if M is trivalent, then only one X-Y group is present; if M is tetravalent, then two X-Y groups are present); and
M=any metal from the Periodic Table with valency greater than 2.

Examples of monovalent metal ions include, but are not limited to, $Na^+$, $K^+$, and $NR_4^+$.

Examples of divalent linking groups include, but are not limited to, O, $CH_2$, NH, COO, CONH, CO, $SO_3$, and $SO_2NH$.

Examples of M include indium, gallium, thallium, germanium, tin, antimony, bismuth, cobalt, nickel, silicon, titanium, titanyl, vanadium, vanadyl, chromium, manganese, yttrium, scandium, zirconium, niobium, molybdenum, ruthenium, rhodium, hafnium, tantalum, or bismuth.

The water-soluble phthalocyanine dye or naphthalocyanine dye with near-infrared absorption comprises from one to three complexed units, each unit comprising a phthalocyanine or a naphthalocyanine moiety. For example, Formulae IV and V each have one such unit. For two or three units, each unit is joined to an adjacent unit through a fused ring, as shown in subsection A above.

A metal atom is complexed to each unit, and each metal atom has a valency of at least three. Two valencies are used in complexing to the phthalocynanine ring or the naphthalocyanine ring. Where the metal atom has a valency of three, this leaves one valency for attachment to a water-soluble ligand. Where the metal atom has a valency of four, this leaves two valencies for attachment, each to a water-soluble ligand (Formulae I-III).

Further, -AB and —C moieties may be attached to the outermost benzene rings and/or the phenyl rings of the PC or NPC group, as shown in Formula (V).

There are two aspects that contribute to increasing the water solubility of the dyes. The first is, as with the increasing water solubility discussed in subsection A above, the addition of axial ligands on the central metal atom. The second aspect is the addition of phenyl groups, attached to the outermost benzene rings of the PC or NPC group, which provides extended conjugation. Further, groups comprising double bonds, such as ethylene, and/or triple bonds, such as acetylene may additionally or alternatively be employed in conjunction with or in place of the phenyl groups.

General Synthetic Process:

First, the NPC derivative with extended conjugation is formed with the central metal M with axial halogen atom(s), hydroxyl or alkoxy groups. Next, it is treated with the water solubilizing groups by nucleophilic substitution reactions, for example, sulfuric acid, polyethylene glycols, and the like materials. Then, the product is purified by conventional purification processes such as column chromatography or crystallization techniques.

C. Considerations Relating to Inks

In addition to the near-infrared absorbing compounds described herein as well as the inks containing such compounds, the present disclosure provides a method of printing such compounds and inks. In one embodiment, a method of printing any of the near-infrared absorbing compounds described herein can comprise printing an ink-jet ink containing the near-infrared absorbing compound with an ink-jet printer.

Generally, ink-jet printers contain ink-jet ink print heads that are used to eject ink droplets accurately at precise locations on print media. As such, ink-jet printers can contain from several nozzles in the print head to more than 400 nozzles. A high population of nozzles can increase the print quality and speed of the ink-jet printing. However, frequently, the nozzles get blocked because of the usage of pigmented inks or inks containing particles, such as binders, resins, latexes, etc. As such, streaks can occur, which leads to poor print quality.

As such, ink-jet printers having near-infrared absorbing compounds in the ink-jet ink can be coupled to a detection system used to monitor nozzle health. Generally, the detection system monitors the ink ejected from the nozzles by detecting the near-infrared absorbing compound in the ink-jet ink. If the detection system fails to detect the near-infrared absorbing compound, the printer can ascertain that such nozzle is blocked or otherwise faulty and adjust the printing by using a different nozzle(s), thereby maintaining print quality and performance.

Additionally, the present ink-jet inks can provide security features. The present near-infrared absorbing compounds can be tailored to absorb specific wave-lengths. Once an ink-jet ink has been manufactured with a near-infrared absorbing compound described herein, such an ink can be characterized by determining the absorption of the ink in the near-infrared wavelength region. After such information is determined and catalogued, the ink-jet ink can be printed and subsequently verified for its particular absorption. The ink could then be used to determine the authenticity of the print.

Additionally, the present near-infrared absorbing compounds can provide increased stability by increasing the extinction coefficient of the near-infrared absorbing compounds. As such, the present near-infrared absorbing compounds allow for an ink-jet ink formulation having a smaller quantity of the near-infrared absorbing compounds, leading to lower production costs.

The inks of the present disclosure can be used with commercially available is ink-jet printers, such as DESKJET® or PHOTOSMART® and other similar printers manufactured by Hewlett-Packard Company. It is notable that these inks are acceptable for use with both thermal ink-jet ink printers and piezo ink-jet printers. They can also be used with off-axis printers, which have a high demand with respect to maintaining a reliable ink with low incidences of dogging. Further, these ink sets can produce true colors on a variety of media, including uncoated media, clay coated media, inorganic porous coated media, e.g., silica- and alumina-based media, and organic swellable media, e.g., gelatin coated media, each with improved light fastness, gamut, and other print quality enhancements.

As previously discussed, the inks of the present invention can include a colorant in the form or a dye and/or pigment. In one embodiment, the ink can be a cyan ink, magenta ink, yellow ink, pale cyan ink, pale magenta ink, green ink, blue ink, orange ink, pink ink, gray ink, etc. Additionally, multiple inks can be used to form an ink set for use with the printers described herein. As such, a printer can have from one to multiple dyes in a single ink, each having more than one dye load, and/or multiple dyes in over an ink set. Some or all of the inks in an ink set can additionally include the near-IR dyes described herein, or an ink might include a near-IR dye described herein without the presence of another colorant. The typical colorant range is about 0.1% to 6% by weight of the total ink composition.

A typical liquid vehicle formulation that can be used with a dye set of the present invention can include one or more organic co-solvent(s), present in total at from 5.0% to 50.0% by weight, and one or more non-ionic, cationic, and/or anionic surfactant(s), present from 0.01% to 10.0% by weight. The balance of the formulation can be purified water, or other vehicle components known in the art such as biocides, viscosity modifiers, pH adjusting agents, sequestering agents, preservatives, anti-kogation agents, bleed control agents, drying agents, jettability agents, and the like.

The concentration of the PC and NPC dyes disclosed herein for use in the foregoing typical formulation ranges from about 0.0001% to 1% by weight of the ink, in addition to colorant (dyes and/or pigments) described above. In some embodiments, the concentration of the PC and NPC dyes may range from about 0.005% to 0.5% by weight of the ink. The concentration of the PC and NPC dyes depends on the extinction coefficient of the dye for detection. If the extinction coefficient of the PC or NPC dye is comparatively high, then a lower dye concentration may be employed and vice versa.

Classes of co-solvents that can be used can include aliphatic alcohols, aromatic alcohols, diols, glycol ethers, polyglycol ethers, caprolactams, form amides, acetamides, and long chain alcohols. Examples of such compounds include primary aliphatic alcohols, secondary aliphatic alcohols, 1,2-alcohols, 1,3-alcohols, 1,5-alcohols, ethylene glycol alkyl ethers, propylene glycol alkyl ethers, higher hornologs ($C_6$-$C_{12}$) of polyethylene glycol alkyl ethers, N-alkyl caprolactams, unsubstituted caprolactams, both substituted and unsubstituted formamides, both substituted and unsubstituted acetamides, and the like. Specific examples of solvents that can be used include 2-pyrrolidinone, derivatized 2-pyrrolidinone including 1-(2-hydroxyethyl)-2-pyrrolidinone, 2-methyl-1,3-propanediol, tetraethylene glycol, and ethylhydroxypropanediol (EHPD), to name a few.

One or more of many surfactants can also be used as are known by those skilled in the art of ink formulation and may be alkyl polyethylene oxides, alkyl phenyl polyethylene oxides, polyethylene oxide block copolymers, acetylenic poly-ethylene oxides, polyethylene oxide (di)esters, polyethylene oxide amines, protonated polyethylene oxide amines, protonated polyethylene oxide amides, dimethicone copolyols, substituted amine oxides, and the like. Specific examples of preferred surfactants for use include SOLSPERSE, TERGITOL, DOWFAX, and the like. The amount of surfactant added to the formulation, if included, may range from 0.01% to 10.0% by weight.

Consistent with the formulation of this invention, various other additives may be employed to optimize the properties of the ink composition for specific applications. Examples of these additives are those added to inhibit the growth of harmful microorganisms. These additives may be biocides, fungicides, and other anti-microbial agents, which are routinely used in ink formulations. Examples of suitable microbial agents include, but are not limited to, NLJOSEPT, LJCARCIDE, VANCIDE, PROXEL, and combinations thereof.

Sequestering agents, such as EDTA (ethylenediaminetetraacetic acid), may be included to eliminate the deleterious effects of metal impurities. Such sequestering agents, if present, typically comprise from 0.01 wt % to 2 wt % of the ink-jet ink compositions. Viscosity modifiers may also be present, as well as other additives known to those skilled in the art to modify properties of the ink as desired. Such additives can be present in the ink-jet ink compositions at from 0 wt % to 20 wt %

Various buffering agents or pH adjusting agents can also be optionally used in the ink-jet ink compositions of the present invention. Typical pH adjusting agents include such pH control solutions as hydroxides of alkali metals and amines, such as lithium hydroxide, sodium hydroxide, potassium hydroxide; citric acid; amines such as triethanolamine, diethanolamine, and dimethyl-ethanolamine; hydrochloric acid; and other basic or acidic components. If used, pH adjusting agents typically comprise less than about 10 wt % of the ink-jet ink composition. Similarly, buffering agents can be used such as, but not limited to, TRIS, MOPS, citric acid, acetic acid, MES, etc. If used, buffering agents typically comprise less than about 3 wt % of the ink-jet ink composition and generally from about 0.01 wt % to 2 wt %, most commonly from 0.2 wt % to 0.5 wt %. Additionally, anti-kogation agents that can be used include lithium phosphate, sodium phosphate, phosphate esters of fatty alcohol alkoxylates, and the like, in amounts from about 0.01 wt % to 5 wt %.

EXAMPLES

Example 1

Preparation of Dimer Compound with Axial Ligand

The following chemicals 1,2,4,5-tetracyanobenzene (2 mmol), 1,2-dicyanonaphthalene (6 mmol), indium chloride (2 mmol), and N,N'-dimethylformamide (0.6 ml) are mixed together along with ammonium molybdate (25 mg) as a catalyst. This mixture is heated to 210° C. for 2 h and cooled to ambient temperature. The product is washed with isopropanol and dried to obtain a dimer of Formula (II) having indium as the central metal atom with chlorine attached.

Example 2

Introduction of Axial Ligand to Compound from Example 1

The compound from Example 1 (1 mmol) is mixed with poly(ethylene glycol) methyl ether of molecular weight 2000 (2 mmol) in pyridine (5 ml). This mixture is heated to 120° C. for up to 24 h, and then cooled. The volatiles are removed to obtain the water-soluble form of Formula (I) in which the axial ligand is a (polyethylene glycol) unit.

Example 3

Water-Soluble Form of Formula (III)

The compound obtained from Example 2 (1 g) is sulfonated by mixing with fuming sulfuric acid having 20°/h sulfur trioxide content (6 ml). This mixture is stirred at room temperature for 24 h. It is poured in crushed ice and the product obtained is filtered and washed with cold water to remove excess sulfuric acid. Finally, the pH of the solution is adjusted to obtain a water-soluble sulfonated form of Formula (III) with the axial ligand as a poly(ethylene glycol) unit.

Example 4

Preparation of NPC with Extended Conjugation Through Phenyl Ring Having Axial Polyethylene glycol) of Formula (IV)

The following ingredients 1-phenyl-2-3-naphthalenedicarboxylic anhydride (1 g), 0.2 grams of indium chloride (0.2 g), p-toluenesulfonic acid (0.14 g), and hexamethyldisilazane (6 g) were mixed and heated to 110° C. for 1 hour. Then, 1 gram of dimethyl formamide was added to the reaction mixture and the reaction mixture was heated to 150° C. for 16 hours. The reaction mixture was cooled and washed with isopropanol. The product obtained from the isopropanol-washed mixture has a central metal atom as indium with chlorine atom attached. This compound (1 mmol) is mixed with poly(ethylene glycol) methyl ether of molecular weight 2000 (2 mmol) in pyridine (5 ml). This mixture is heated to 120° C. for 6 h and then cooled. The volatiles are removed to obtain water soluble form of Formula (IV) in which the axial ligand is a poly(ethylene glycol) unit.

Example 5

Water-Soluble Form of Formula (IV)

The compound from Example 4 (1 g) is sulfonated by mixing with fuming sulfuric acid having 20% sulfur trioxide content (6 ml). This mixture is stirred at room to temperature for 24 h. It is poured in crushed ice and the product obtained is and washed with water to remove excess sulfuric acid. Finally, the pH of the solution is adjusted to obtain a water-soluble sulfonated form of Formula (IV) with the axial ligand as a polyethylene glycol) unit.

What is claimed is:

1. A water-soluble phthalocyanine dye or naphthalocyanine dye with near-infrared absorption comprising at least one complexed unit, each unit comprising a phthalocyanine or a naphthalocyanine moiety and a metal atom complexed thereto, each metal atom having a valency of at least four, with two valencies complexed to the phthalocynanine ring or the naphthalocyanine ring, each unit joined to another through a fused ring, at least two valencies attached to water-soluble axial ligands, wherein the water-soluble axial ligands are X-Y groups, where X=single bond, O or NH; Y=COOZ, $SO_3Z$, $PO_3Z$, $(CH_2CH_2O)_mCH_3$, $(CH_2CH(CH_3)O)_mCH_3$, $(CH_2CH_2S)_mCH_3$ or $(CH_2CH(CH_3)S)_mCH_3$; m=1 to 500; and Z=H or monovalent metal ions.

2. The dye of claim 1 comprising from two to four complexed units.

3. The dye of claim 2 further including ligands attached to at least one benzene or naphthylene ring of the phthalocyanine or naphthalocyanine dye.

4. The dye of claim 2 selected from the group consisting of phthalocyanine dyes and naphthalocyanine dyes having water-soluble axial ligands having a general structure given by any of Formulae (I), (II) or (III):

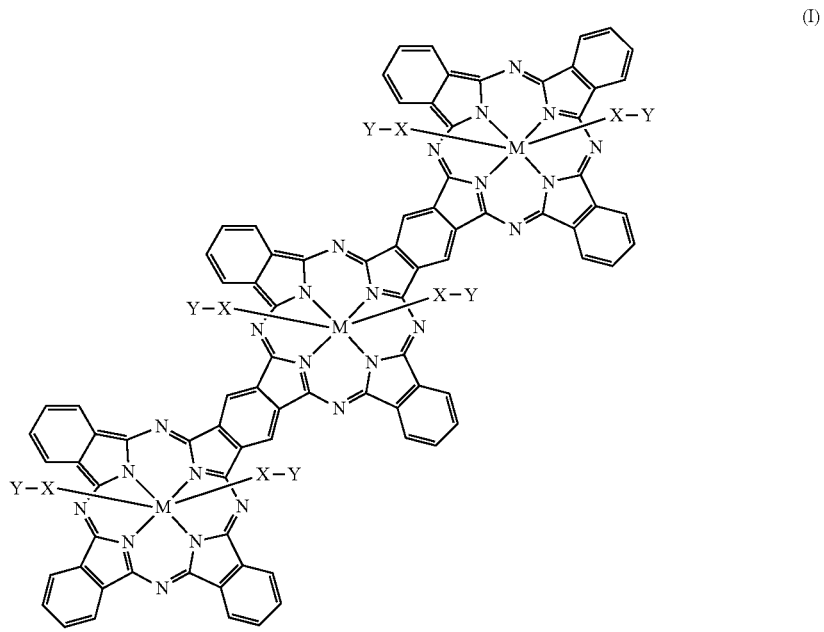

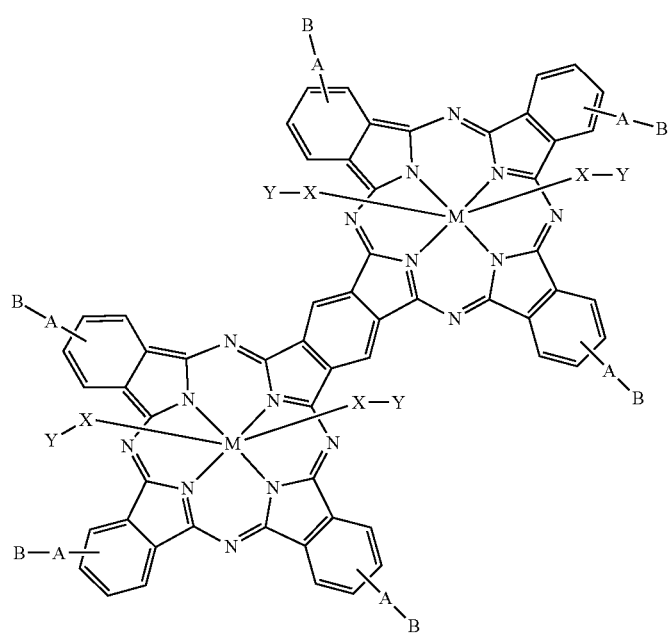
(II)
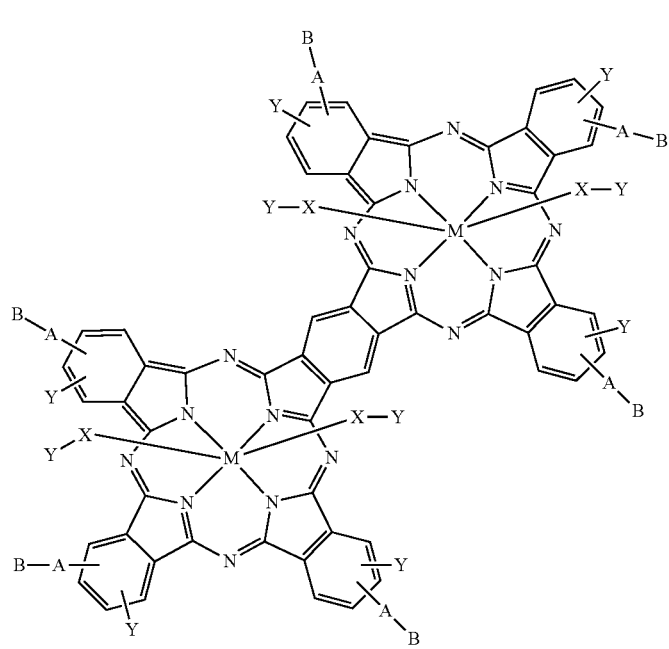
(III)
where:
X=single bond, O or NH;
Y=COOZ, SO₃Z, PO₃Z, (CH₂CH₂O)$_m$CH₃, (CH₂CH(CH₃)O)$_m$CH₃, (CH₂CH₂S)$_m$CH₃ or (CH₂CH(CH₃)S)$_m$CH₃; m=1 to 500;
Z=H or monovalent metal ions;
A=a divalent linking group;
B=H, alkyl or substituted alkyl;
the number of X-Y groups depends upon the valency of the metal atom M; and
M=any metal from the Periodic Table with valency greater than 3.

5. The dye of claim 1 comprising from one to three complexed units.

6. The dye of claim 5 further including at least one moiety providing extended conjugation attached to at least one benzene or naphthylene ring of the phthalocyanine or naphthalocyanine dye.

7. The dye of claim 6 wherein the at least one moiety is selected from the group consisting of phenyl rings, double bonds, and triple bonds.

8. The dye of claim 5 further including ligands attached to at least one benzene or naphthylene ring of the phthalocyanine or naphthalocyanine dye, attached to the at least one phenyl group, or attached to both at least one benzene or naphthylene ring of the phthalocyanine or naphthalocyanine dye and the at least one phenyl group.

9. The dye of claim 5 selected from the group consisting of phthalocyanines and naphthalocyanines having extended conjugation and water-soluble axial ligands having a general structure given by Formula (IV):

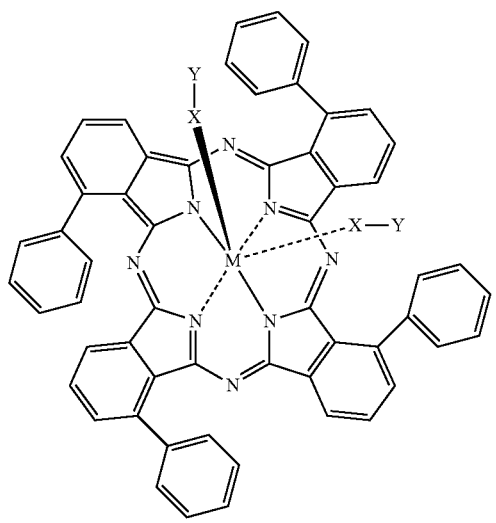

(IV)

where:
X=single bond, O or NH;
Y=COOZ, SO$_3$Z, PO$_3$Z, (CH$_2$CH$_2$O)$_m$CH$_3$, (CH$_2$CH(CH$_3$)O)$_m$CH$_3$, m=1 to 500;
Z=H or monovalent metal ions;
A=a divalent linking group;
B=substituent C=H, alkyl or substituted alkyl;
the number of X-Y groups depends upon the valency of the metal atom M; and
M=any metal from the Periodic Table with valency greater than 3.

10. The dye of claim 6 wherein Z is selected from the group consisting of Na$^+$ and K$^+$.

11. The dye of claim 6 wherein the divalent linking group is selected from the group consisting of O, CH$_2$, NH, COO, CONH, CO, SO$_3$, and SO$_2$NH.

12. The dye of claim 6 wherein M is indium, gallium, thallium, germanium, tin, antimony, bismuth, zinc, cobalt, nickel, silicon, titanium, vanadium, chromium, manganese, yttrium, scandium, zirconium, niobium, molybdenum, ruthenium, rhodium, hafnium, tantalum, or bismuth.

13. The dye of claim 12 wherein M is indium, gallium, or thallium.

14. The dye of claim 5 selected from the group consisting of phthalocyanines and naphthalocyanines having extended conjugation and water-soluble axial ligands having a general structure given by Formula (V):

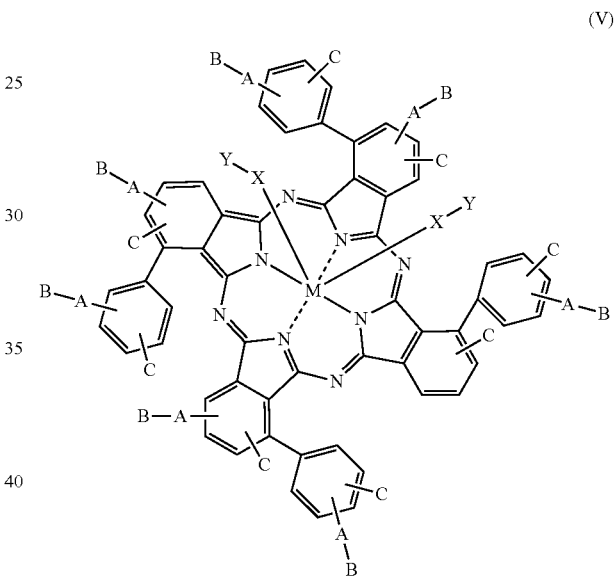

(V)

where:
X=single bond, O or NH;
Y=COOZ, SO$_3$Z, PO$_3$Z, (CH$_2$CH$_2$O)$_m$CH$_3$, (CH$_2$CH(CH$_3$)O)$_m$CH$_3$, (CH$_2$CH$_2$S)$_m$CH$_3$ or (CH$_2$CH(CH$_3$)S)$_m$CH$_3$; m=1 to 500;
Z=H or monovalent metal ions;
A=a divalent linking group;
B=substituent C=H, alkyl or substituted alkyl;
the number of X-Y groups depends upon the valency of the metal atom M; and
M=any metal from the Periodic Table with valency greater than 3.

15. An inkjet ink formulation comprising:
(a) an aqueous vehicle;
(b) at least one dye or pigment; and
(c) the dye of claim 1.

* * * * *

UNITED STATES PATENT AND TRADEMARK OFFICE
CERTIFICATE OF CORRECTION

PATENT NO. : 8,808,439 B2  Page 1 of 1
APPLICATION NO. : 13/383724
DATED : August 19, 2014
INVENTOR(S) : Sivapackia Ganapathiappan et al.

It is certified that error appears in the above-identified patent and that said Letters Patent is hereby corrected as shown below:

In the Claims

Column 14, line 17, Claim 1, delete "phthalocynanine" and insert -- phthalocyanine --, therefor.

Column 17, line 57, Claim 9, before "m=1 to 500;"
insert -- $(CH_2CH_2S)_mCH_3$ or $(CH_2CH(CH_3)S)_mCH_3$; --.

Column 17, line 61, Claim 9, delete "C═H," and insert -- C=H, --, therefor.

Column 18, line 54, Claim 14, delete "C═H," and insert -- C=H, --, therefor.

Signed and Sealed this
Tenth Day of February, 2015

Michelle K. Lee
*Deputy Director of the United States Patent and Trademark Office*